US009145582B2

(12) United States Patent
Mourelatos et al.

(10) Patent No.: US 9,145,582 B2
(45) Date of Patent: Sep. 29, 2015

(54) MICROARRAY TECHNIQUES FOR NUCLEIC ACID EXPRESSION ANALYSES

(75) Inventors: Zissimos Mourelatos, Philadelphia, PA (US); Peter T. Nelson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1169 days.

(21) Appl. No.: 11/232,820

(22) Filed: Sep. 22, 2005

(65) Prior Publication Data

US 2006/0078925 A1    Apr. 13, 2006

Related U.S. Application Data

(60) Provisional application No. 60/612,301, filed on Sep. 22, 2004.

(51) Int. Cl.
    *C12Q 1/68*    (2006.01)
(52) U.S. Cl.
    CPC ............ *C12Q 1/6809* (2013.01); *C12Q 1/6837* (2013.01)
(58) Field of Classification Search
    None
    See application file for complete search history.

(56) References Cited

U.S. PATENT DOCUMENTS

| | | | | |
|---|---|---|---|---|
| 4,851,331 | A * | 7/1989 | Vary et al. | 435/6 |
| 5,512,439 | A * | 4/1996 | Hornes et al. | 435/6 |
| 6,277,579 | B1 * | 8/2001 | Lazar et al. | 435/6 |
| 2003/0027161 | A1 * | 2/2003 | Bejanin et al. | 435/6 |
| 2003/0198979 | A1 * | 10/2003 | Cho et al. | 435/6 |
| 2006/0166203 | A1 * | 7/2006 | Tooke | 435/6 |
| 2007/0077562 | A1 * | 4/2007 | Hossain et al. | 435/6 |

OTHER PUBLICATIONS

Nordstrom et al. (Biotechnol Appl Biochem 2000 vol. 31 p. 107).*
Bai et al. PNAS 2003 vol. 100 p. 409.*
Allawi, T H. et al., "Quantitation of microRNAs using a modified Invader assay," *RNA*, 10:1153-1161 (2004).
Ambros, V. et al., "A uniform sytem for microRNA annotation," *RNA*, 9:277-279 (2003).
Bartel, P. D. et al., "MicroRNAs: Genomics, Biogenesis, Mechanism, and Function," *Cell*, 116:281-297 (2004).
Brody, S. R. et al., "Processivity and Kinetics of the Reaction of Exonuclease I from *Escherichia coli* with Polydeoxyribonucleotides," *The Journal of Bio. Chem.*, 261(16):7136-7143 (1986).
Calin, G. A. et al., "MicroRNA profiling reveals distinct signatures in B cell Chronic lymphocytic leukemias," *PNAS*, 101(32):11755-11760, 2004.
Calin, G. et al., Frequent Deletions and Down-Regulation of Micro-RNA Genes miR15 and miR16 at 13q14 in Chronice Lymphocytic, PNAS 2002 vol . 99 p. 15524-15529.

Carrington, C. James, "Role of MicroRNAs in Plant and Animal Development," *Science*, 301:336-338 (2003).
Chiu, Ya-Lin et al., "RNAi in Human Cells: Basic Structural and Functional Features of Small Interfering RNA," *Molecular Cell*, 10:549-561 (2002).
Dai, H. et al., "Use of hybridization kinetics for differentiating specific from non-specific binding to oligonucleotide microarrays," *Nucleic Acids Research*, 30(16):e86 1-8 (2002).
Dorris, R. D. et al., "Oligodeoxyribonucleotide probe accessibility on a three-dimensional DNA microarray surface and the effect of hybridization time on the accuracy of expression ratios," *BMC Biotechnology*, 3(6):1-11 (2003).
Fantroussi, Said El et al., "Direct Profiling of Environmental Microbial Populations by Thermal Dissociation Analysis of Native rRNAs Hybridized to Oligonucleotide Microarrays," *Appl. Environ. Microbiol.*, 69(4):2377-2382 (2003).
Gillis, S. et at et., "Biochemical and Biological Characterization of Lymphocyte Regulatory Molecules," *J. Exp. Med.*, 152:P1709-1719 (1980).
Griffiths-Jones, Sam, "The microRNA Registry," *Nucleic Acids Research*, 32:D109-D111 (2004).
Guschin, Y. D. et al., "Oligonucleotide Microchips as Genosensors for Determinative and Environmental Studies in Microbiology," *Appl. Environ. Microbiol.*, 63(6):2397-2402 (1997).
Head, R. S. et al., "Nested genetic bit analysis (N-GBA) for mutation detection in the p53 tumor suppressor gene," *Nucleic Acid Research*, 25(24):5065-5071 (1997).
Huang Z. et al., "Selective labeling and detection of specific mRNA in a total-RNA sample," *Analytical Biochemistry*, 322:269-274 (2003).
Huang Z. et al., "A simple method for 3'-labeling of RNA," *Nucleic Acids Research*, 24(21):4360-4361 (1996).
Koizumi, Y. et al., "Parallel Characterization of Anaerobic Toluene- and Ethylbenzene-Degrading Microbial Consortia by PCR-Denaturing Gradiant Gel Electrophoresis, RNA-DNA Membrane Hybridization, and DNA Microarray Technology," *Appl. Environ. Microbiol.*, 68(7):3215-3225 (2002).
Korbler, T. et al., "A simple method for RNA isolation from formalin-fixed and paraffin-embedded lymphatic tissues," *Experimental and Molecular Pathology*, 74:336-340 (2003).
Krichevsky, M. A. et al., "A microRNA array reveals extensive regulation of microRNAs during brain development," *RNA*, 9:1274-1281 (2003).

(Continued)

*Primary Examiner* — Katherine Salmon
(74) *Attorney, Agent, or Firm* — Riverside Law LLP

(57) ABSTRACT

Provided are DNA microarray techniques that allow hybridization without RNA amplification, without using cDNA, and without labeling the nucleic acid prior to hybridization. Referred to as the Double-stranded Exonuclease Protection (DEP) assay, the technique permits the sample RNA to be used directly for hybridization, without manipulation in any way. Further provided is a microarray technique for high-throughput miRNA gene expression analyses, termed the RNA-primed, Array-based, Klenow Enzyme (RAKE) assay. The RAKE assay is a sensitive and specific technique for assessing single-stranded DNA and RNA targets, and offers specific advantages over Northern blots.

19 Claims, 8 Drawing Sheets

(56) References Cited

OTHER PUBLICATIONS

Kiriakidou, M. et al., "A combined computational-experimental approach predicts human microRNA targets," *Genes & Development*, 18:1165-1178 (2004).

Lagos-Quintana, M. et al., "Identification of Novel Genes Coding for Small Expressed RNAs," *Science*, 294:853-86 (2001).

Lee, R. et al., "A Short History of a Short RNA," *Cell*, S116:S89-S92 (2004).

Lee, Y. et al., "The nuclear RNase III Drosha Initiates microRNA processing," *Nature*, 425:415-419 (2003).

Lim, P. L. et al., "The microRNAs of Caenorhabditis elegans," *Gene & Development*, 17:991-1008 (2003).

Liu, Chang-Gong et al., "An oligonucleotide microchip for genome-wide microRNA profiling in human and mouse tissues," *PNAS*, 101(26):9740-9744 (2004).

Liu, Wen-Tso et al., "Optimization of an oligonucleotide microchip for microbial identification studies: a non-equilibrium dissociation approach," *Environmental Microbiology*, 3(10):619-629 (2001).

Metzler et al., "High Expression of Precursor MicroRNA-155/BIC RNA in Children with Burkitt Lymphoma," *Genes, Chromosomes & Cancer*, 39:167-169 (2004).

Michael, Z. M. et al., "Reduced Accumulation of Specific MicroRNAs in Colorectal Neoplasia," *Molecular Cancer Research*, 1:882-891 (2003).

Miska, A. E. et al., "Microarray analysis of microRNA expression in the developing mammalian brian," *Genome Biology*, 5:R68 (2004).

Mourelatos, Z. et al., "miRNPs: a novel class of ribonucleoproteins containing numerous microRNAs," *Genes & Development*, 16:720-728 (2002).

Murchison, P. E. et al., "miRNAs on the move: miRNA biogenesis and the RNAi machinery," *Current Opinion in Cell Biology*, 16:223-229 (2004).

Nelson, T. P. et al., "miRNP:mRNA association in polyribosomes in a human neuronal cell line," *RNA*, 10:387-394 (2004).

Nelson, P. et al., "The microRNA world: small is mighty," *Trends in Biochemical Sciences*, 28(10):534-540 (2003).

Nikiforov, T. T. et al., "Genetic Bit Analysis: a solid phase method for typing single nucleotide polymorphisms," *Nucleic Acids Research*, 22(20):4167-4175 (1994).

Ohtsuka, E. et al., "Joining of Synthetic Ribotrinucleotides with Defined Sequences Catalyzed by T4 RNA Ligase," *Eur. J. Biochem.*, 81:285-291 (1977).

Ramakrishnan, R. et al., "An assessment of Motorola CodeLink™ microarray performance for gene expression profiling applications," *Nucleic Acids Research*, 30(7):e30 (2002).

Romaniuk, E. et al., "The Effect of Acceptor Oligoribonucleotide Sequence on the $T_4$ RNA Ligase Reaction," *Eur. J. Biochem.*, 125:639-643 (1982).

Ruvkun, G. et al., "The 20 Years it Took to Recognize the Importance of Tiny RNAs," *Cell*, S116:S93-S96 (2004).

Schmittgen, D. T. et al., "A high-throughput method to monitor the expression of microRNA precursors," *Nucleic Acids Research*, 32(4):e43 (2004).

Sempere, F. L., "Expression profiling of mammalian microRNAs uncovers a subset of brain-expressed microRNAs with possible roles in murine and human neuronal differentiation," *Genome Biology*, 5:R13 (2004).

Takamizawa, J. et al., "Reduced Expression of the *let-7* MicroRNAs in Human Lung Cancers in Association with Shortened Postoperative Survival," *Cancer Research*, 64:3753-3756 (2004).

Urakawa, H. et al., "Optimization of Single-Base-Pair Mismatch Discrimination in Oligonucleotide Microarrays," *Appl. Environ. Microbiol.*, 69(5):2848-2856 (2003).

Van Deerlin, V. et al., "Optimizing Gene Expression Analysis in Archival Brain Tissue," *Neurochemical Research*, 27(10):993-1003 (2002).

\* cited by examiner

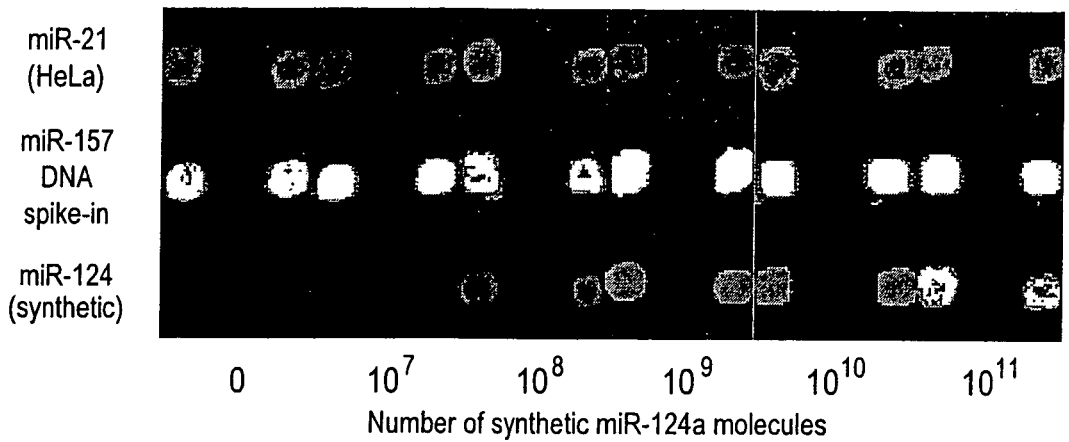
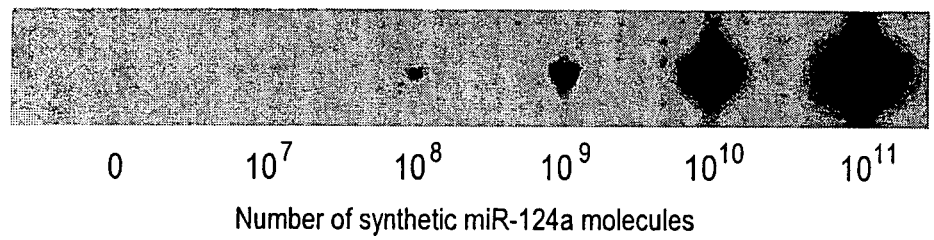
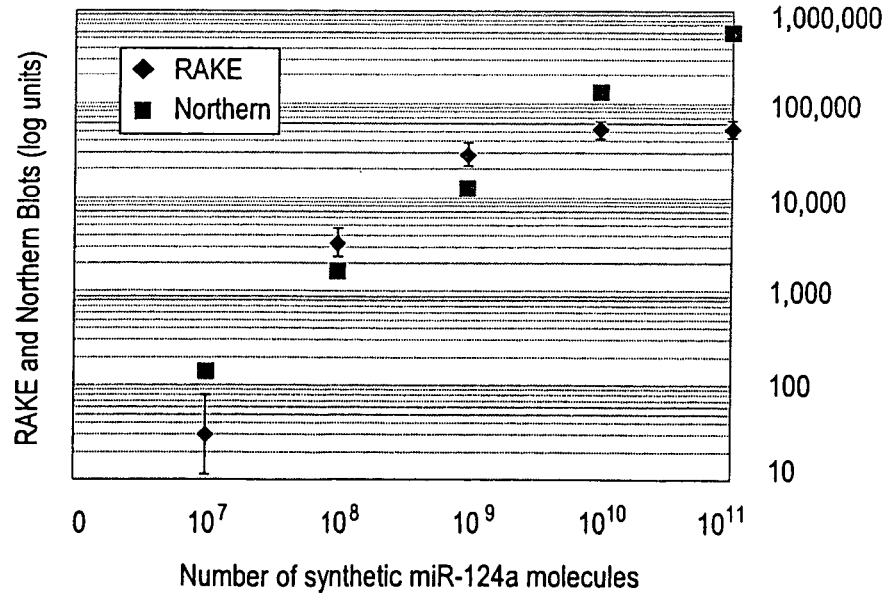
Figure 2

| Sample | miRNA |
|---|---|
| PF OOMHJ | |
| | hsa-let-7bL |
| | hsa-let-7bL |
| | hsa-let-7cL |
| | hsa-let-7dL |
| | hsa-let-7eL |
| | hsa-let-7f |
| | hsa-mir-100 |
| | hsa-mir-101 |
| | hsa-mir-102-1,2,3 |
| | hsa-mir-103-1,2 |
| | hsa-mir-104 |
| | hsa-mir-105-1,2 |
| | hsa-mir-106 |
| | hsa-miR-106b |
| | hsa-mir-107 |
| | hsa-mir-10a |
| | hsa-mir-124b |
| | hsa-miR-127 |
| | hsa-mir-130 |
| | hsamiR-130b |
| | hsa-mir-139 |
| | hsa-miR-141 |
| | hsa-miR-142 3p |
| | hsa-miR-142 5p |
| | hsa-miR-143a |
| | hsa-mir-147 |
| | hsa-mir-148 |
| | hsa-mir-15a |
| | hsa-mir-16 |
| | hsa-mir-17 |
| | hsa-mir-18 |
| | hsa-mir-181a |
| | hsa-mir-181b |
| | hsa-mir-181c |
| | hsa-mir-182-as |
| | hsa-mir-183 |
| | hsa-mir-187 |
| | hsa-mir-192 |
| | hsa-mir-196-1,2 |
| | hsa-mir-197 |
| | hsa-mir-198 |
| | hsa-miR-199a* |
| | hsa-mir-199a-1 |
| | hsa-mir-199b |
| | hsa-mir-19a |
| | hsa-mir-19b-1,2 |
| | hsa-mir-20 |
| | hsa-mir-200b |
| | hsa-mir-203 |
| | hsa-mir-205 |
| | hsa-mir-208 |
| | hsa-miR-21 |
| | hsa-mir-210 |
| | hsa-mir-211 |
| | hsa-mir-212 |
| | hsa-mir-213 |
| | hsa-mir-214 |
| | hsa-mir-215 |
| | hsa-mir-216 |
| | hsa-mir-217 |
| | hsa-mir-218-1,2 |
| | hsa-mir-219 |
| | hsa-mir-22 |
| | hsa-mir-220 |
| | hsa-mir-221 |
| | hsa-mir-222 |
| | hsa-mir-223 |
| | hsa-mir-224 |
| | hsa-miR-23a |
| | hsa-miR-23b |
| | hsa-mir-24-1,2 |
| | hsa-mir-25 |

| Sample | miRNA |
|---|---|
| PF OOMHJ | |
| | hsa-mir-26a |
| | hsa-mir-26b |
| | hsa-mir-27 |
| | hsa-mir-28 |
| | hsa-mir-29 |
| | hsa-miR-299 |
| | hsa-mir-30a |
| | hsa-mir-30a-as |
| | hsa-mir-30c |
| | hsa-mir-30d |
| | hsa-mir-31 |
| | hsa-miR-302a |
| | hsa-mir-32 |
| | hsa-mir-320 |
| | hsa-mir-321 |
| | hsa-mir-33 |
| | hsa-mir-34 |
| | hsa-miR-34b |
| | hsa-mir-7 |
| | hsa-mir-9 |
| | hsa-mir-9* |
| | hsa-mir-91 |
| | hsa-mir-92-1,2 |
| | hsa-miR-93 |
| | hsa-mir-95 |
| | hsa-mir-98 |
| | hsa-mir-99 |
| | hsa-miR-99b |
| | mmu-let-7d* |
| | mmu-let-7gL |
| | mmu-let-7iL |
| | mmu-mir-101 |
| | mmu-mir-10b |
| | mmu-miR-106a |
| | mmu-miR-106b |
| | mmu-mir-122a |
| | mmu-mir-124a |
| | mmu-mir-125a |
| | mmu-mir-125b |
| | mmu-mir-126 |
| | mmu-mir-128 |
| | mmu-mir-129b |
| | mmu-mir-132 |
| | mmu-mir-133 |
| | mmu-mir-134 |
| | mmu-mir-135 |
| | mmu-mir-136 |
| | mmu-mir-137 |
| | mmu-mir-138 |
| | mmu-mir-140 |
| | mmu-mir-142-as |
| | mmu-mir-142-s |
| | mmu-mir-143 |
| | mmu-mir-144 |
| | mmu-mir-145 |
| | mmu-mir-146 |
| | mmu-mir-149 |
| | mmu-mir-150 |
| | mmu-mir-151 |
| | mmu-mir-152 |
| | mmu-mir-153 |
| | mmu-mir-154 |
| | mmu-mir-155 |
| | mmu-mir-15b |
| | mmu-mir-182 |
| | mmu-mir-184 |
| | mmu-mir-185 |
| | mmu-mir-186 |
| | mmu-mir-188 |
| | mmu-mir-189 |

| Sample | miRNA |
|---|---|
| PF OOMHJ | |
| | mmu-mir-190 |
| | mmu-mir-191 |
| | mmu-mir-193 |
| | mmu-mir-194 |
| | mmu-mir-195 |
| | mmu-mir-1d |
| | mmu-mir-200b |
| | mmu-mir-201 |
| | mmu-mir-202 |
| | mmu-mir-204 |
| | mmu-mir-206 |
| | mmu-mir-207 |
| | mmu-mir-23b |
| | mmu-mir-27b |
| | mmu-mir-29b |
| | mmu-miR-290 |
| | mmu-miR-291 3p |
| | mmu-miR-291 5p |
| | mmu-miR-292 3p |
| | mmu-miR-292 5p |
| | mmu-miR-293 |
| | mmu-miR-294 |
| | mmu-miR-295 |
| | mmu-miR-296 |
| | mmu-miR-297 |
| | mmu-miR-298 |
| | mmu-miR-29b |
| | mmu-miR-300 |
| | mmu-mir-30b |
| | mmu-mir-30e |
| | mmu-miR-34a |
| | mmu-miR-34c |
| | mmu-mir-9 |
| | mmu-miR-96 |
| | mmu-mir-99a |
| | mmu-mir-99b |
| | rno-miR-129* |
| | rno-miR-140* |
| | rno-miR-148b |
| | rno-miR-151* |
| | rno-miR-301 |
| | rno-miR-322 |
| | rno-miR-323 |
| | rno-miR-324-5p |
| | rno-miR-325 |
| | rno-miR-326 |
| | rno-miR-327 |
| | rno-miR-328 |
| | rno-miR-329 |
| | rno-miR-330 |
| | rno-miR-331 |
| | rno-miR-333 |
| | rno-miR-335 |
| | rno-miR-336 |
| | rno-miR-337 |
| | rno-miR-338 |
| | rno-miR-339 |
| | rno-miR-340 |
| | rno-miR-341 |
| | rno-miR-342 |
| | rno-miR-343 |
| | rno-miR-344 |
| | rno-miR-345 |
| | rno-miR-346 |
| | rno-miR-347 |
| | rno-miR-349 |
| | rno-miR-350 |
| | rno-miR-351 |
| | rno-miR-352 |
| | rno-miR-7 |

Figure 5

A Figure 8A
| hsa-miR-23a | AUCACAUUGCCAGGGAUUUCC |
| hsa-miR-23b | AUCACAUUGCCAGGGAUUACC<u>AC</u> |
| | |
| hsa-miR-27a | UUCACAGUGGCUAAGUUCCGCC |
| hsa-miR-27b | UUCACAGUGGCUAAGUUCUG |
| | |
| hsa-miR-200b | CUCUAAUACUGCCUGGUAAUGAUG |
| mmu-miR-200b | UAAUACUGCCUGGUAAUGAUG<u>AC</u> |
Figure 8B
B
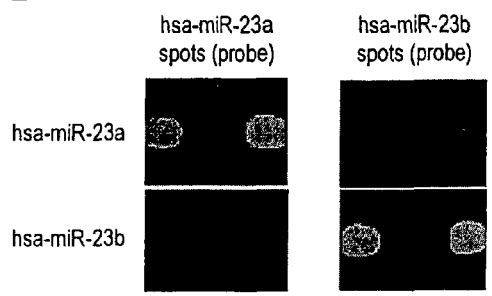
D
|  | RAKE | Northern |
|---|---|---|
|  | 23a/23b | |
| hsa-miR-23a | 13.9 | 1.44 |
| hsa-miR-23b | 0.08 | 0.85 |
|  | 27a/27b | |
| hsa-miR-27a | 13.3 | 2.32 |
| hsa-miR-27b | <0.001 | 0.22 |
|  | hsa/mmu | |
| hsa-miR-200b | 2.10 | 1.12 |
| mmu-miR-200b | 0.07 | 0.51 |
C
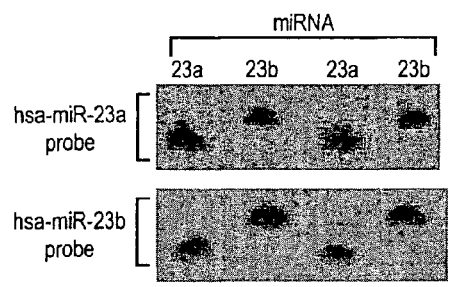
Figure 8C
Figure 8D

MICROARRAY TECHNIQUES FOR NUCLEIC ACID EXPRESSION ANALYSES

CROSS-REFERENCE TO RELATED APPLICATIONS

The present application claims priority to U.S. Provisional Patent Application No. 60/612,301, filed Sep. 22, 2004, the content of which is incorporated herein by reference.

GOVERNMENT INTERESTS

The present invention was supported in part by U.S. National Institutes of Health Training Grant T32-AG00255. The government may have certain rights in the invention.

FIELD OF THE INVENTION

The invention relates to the field of microarray techniques.

BACKGROUND OF THE INVENTION

RNA expression profiling is used to characterize the RNA species present in a sample. Many different techniques are used for this task, each having its own strengths and weaknesses. DNA microarrays are one of the best 'high-throughput' techniques for RNA expression profiling. However, most DNA microarrays require extensive sample manipulation. Specifically, sample RNA must be reversed-transcribed into cDNA, then amplified and labeled with one or more fluorophores prior to array hybridization. As a result, biases may be introduced in any of these steps that may artificially skew the results of the microarray analysis. In addition, the current microarray technology is limited in that it is designed to detect only mRNAs.

A major fraction of cellular RNAs, comprise noncoding RNAs, many of which have regulatory functions. Detection of these noncoding RNAs require (or would benefit from) development of novel microarray technology that would not require sample RNA amplification or labeling. Such technology would be desirable, for example, in the detection of microRNAs (miRNAs).

MicroRNAs are small (~22 nucleotide) regulatory RNAs, that are found in the vast majority of eukaryotic cells. MiRNAs play important roles in plant and animal development, apoptosis, fat metabolism, growth control and hematopoietic differentiation (Lee et al., *Cell* 116 S89-92, 81 p following S96 (2004); Ruvkun et al., *Cell* 116, S93-96, 92 p following S96 (2004); Lagos-Quintana et al., *Science* 294:853-858 (2001); Bartel et al., *Cell* 116:281-297 (2004); Nelson et al., *Trends Biochem. Sci.* 28:534-540 (2003); Carrington et al., *Science* 301:336-338 (2003)). Dysregulation of miRNAs may contribute to human disease including cancer Calin et al., *Proc. Natl. Acad. Sci. USA* 99:15524-15529 (2002); Michael et al., *Mol. Cancer Res.* 1:882-891 (2003); Takamizawa et al., *Cancer Res.* 64:3753-3756 (2004)).

Many individual miRNAs are conserved across widely diverse phyla, indicating their physiological importance. More than 200 miRNAs have been reported thus far from mammals, and miRNAs are estimated to account for ~1.0% of expressed human genes (Bartel et al., 2004). Most animal miRNAs have the capacity to regulate multiple mRNA targets (Kiriakidou et al., *Genes Dev.* 18(10); 1165-1178 (2004); reviewed in Bartel et al., 2004). Yet such RNAs cannot be studied using conventional microarray-based techniques.

In mammalian cells, primary miRNA transcripts (pri-miR-NAs) are cleaved sequentially in the cell nucleus and transported to the cytoplasm (as pre-miRNAs) where mature miR-NAs are generated (Lee et al. *Nature* 425: 415-419 (2003)). Mature miRNAs guide regulatory proteins to induce translational repression or degradation of specific target mRNAs (Bartel et al., 2004; Murchison et al., *Curr. Opin. Cell Biol.* 16:223-229 (2004)).

High-throughput miRNA gene expression analysis has proven to be technically challenging. The short length and uniqueness of each miRNA render many conventional tools ineffective. Very small RNAs are difficult to reliably amplify or label without introducing bias (Ohtsuka et al. *Eur. J. Biochem.* 81:285-291 (1977); Romaniuk et al. *Eur. J Biochem.* 125:639-643 (1982)). Prior attempts at systematic gene expression analysis have involved dot-blots (Krichevsky et al., *RNA* 9:1274-1281 (2003)) or Northern blots (e.g., Sempere et al., *Genome Biol.* 5:R13 (2004); Lim et al., *Genes Dev.* 17:991-1008 (2003)). Additional assays for sensitive detection of miRNAs or their precursors have been developed, involving realtime quantitative PCR-based analysis of pre-miRNA expression (Schmittgen et al., *Nucleic Acids Res.* 32:e43 (2004)), or a modification of the Invader assay for miRNA detection and quantitation (Allawi et al., *RNA* 10:1153-1161 (2004).

While Northern blots are currently the gold standard of miRNA validation and quantification (Ambros et al., *RNA* 9:277-279 (2003)), the specificity of the Northern blot technique has received scant critical review. This is surprising considering the widespread use of the method. Short DNA/RNA hybrids demonstrate $T_m$ and binding dynamics that vary significantly with probe and target nucleotide composition, buffer contents, and the time and temperature of hybridization (Dai et al., 2002; Liu et al, 2001; Dorris et al., 2003; Urakawa et al., *Appl. Environ. Microbiol.* 69:2848-2856 (2003); Guschin et al., *Appl. Environ. Microbiol.* 63:2397-2402 (1997)). Thus, it is highly probable that "signal intensity" for Northern blots will vary from one miRNA sample to another, as well as from one experiment to another. Moreover, standard Northern blotting does not provide absolute quantification, meaning that each RNA queried must include a standard curve in order to be considered "absolutely quantitative," and each standard curve must further be run in parallel with each individual experiment (Lim et al., 2003, supra).

Because higher-throughput techniques involving mature miRNAs are needed to further understand the role(s) played by miRNAs in normal and disease tissues, two groups have reported work on microarrays for miRNAs. Croce and colleagues reported an oligonucleotide microarray for miRNA and pre-miRNA profiling (Liu et al., *Proc. Natl. Acad. Sci. USA* 26:9740-9744 (2004); Liu et al., *Proc. Natl. Acad. Sci. USA* 32:11755-11760 (2004)), wherein the assay involves the use of a biotinylated primer containing a random octamer sequence at the 3'-end. The Liu et al. primer is used, along with reverse transcriptase, to generate a cDNA library from total RNA. The cDNA is isolated and applied to a microarray containing covalently linked DNA oligonucleotide probes corresponding to 245 human and mouse miRNAs (Liu et al., 2004). Horvitz and colleagues also prepared cDNAs from miRNAs using techniques previously employed for the cloning of miRNAs. This was accomplished by ligating adapters to miRNAs using T4 RNA ligase, followed by R.T-PCR using fluorescently-labeled primers complementary to the adapters (Miska et al., *Genome Biol.* 5:R68 (2004)). However, while these reported microarray techniques allow for sensitive, specific and high-throughput miRNA expression profiling, e.g., Miska et al., reported a sensitivity of 0.1 fmoles), but the technique also requires PCR amplification of the miRNA sample.

Nevertheless, much remains unknown about miRNA biology. For example, the miRNA genes expressed in most tissues, species, and cell lines, are not known, and the physiological functions-and regulation-of almost all miRNAs remain to be determined. MiRNAs may also play roles in human disease that have not yet been explored. These and other topics will be easier to address experimentally when miRNA gene expression studies become more feasible, and a need in the art has remained until the present invention for simple and reliable DNA microarray techniques that allow for hybridization without RNA amplification or degredation, without the cumbersome steps involved in making and using cDNA, and without the need to label the nucleic acid prior to hybridization.

SUMMARY OF THE INVENTION

The present invention fulfills this need, among others by providing DNA microarray techniques that allow hybridization without RNA amplification, without using cDNA, and without labeling the nucleic acid prior to hybridization. Referred to as the Double-stranded Exonuclease Protection (DEP) assay, the technique permits the sample RNA to be used directly for hybridization, without manipulation in any way. This eliminates biases introduced during sample RNA manipulation using conventional microarray technology, and greatly facilitates experimentation, wherein the novel microarray technology may be used for the detection of any RNA (including mRNAs and other noncoding RNAs).

Further provided, is a second novel microarray technique for high-throughput miRNA gene expression analyses, termed the RNA-primed, Array-based, Klenow Enzyme (RAKE) assay. The RAKE assay is a sensitive and specific technique for assessing single-stranded DNA and RNA targets, with specific advantages over Northern blots. Moreover, this assay may be modified to have broader applications, e.g., RNA profiling, including profiling and quantification of viruses. The availability of the novel techniques permits, for the first time, a robust sampling of miRNAs made from formalin-fixed, paraffin-embedded (FFPE) pathological samples, followed by expression analysis with RAKE.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE DRAWINGS

FIGS. 2A-2C show the sensitivity and dynamic range of RAKE, and provide a comparison to matching Northern blots. FIG. 2A shows that indicated molecules of a synthetic miRNA (miR-124a, not expressed in HeLa cells) were added to a "complex RNA mixture" derived from low molecular weight HeLa RNAs ($10^8$ molecules=0.16 fmoles). A DNA oligonucleotide corresponding to a plant miRNA (miR-157; not found in HeLa cells) was also added at a constant concentration, as a 'spike-in.' In the data shown in FIG. 2B, the same number of miR-124a molecules were resolved on a 20% denaturing polyacrylamide gel and analyzed by Northern blots. FIG. 2C graphically quantification and comparison of sensitivity between RAKE and Northerns. For RAKE, the signal was defined as the median of foreground spot fluorescence at 532 nm wavelength minus background (defined by surrounding pixel intensity). Negative data values were normalized to zero, but not otherwise normalized. Each concentration point (solid diamond) represents the mean from 12 spots (two microarray slides with six spots per miRNA on each microarray. Standard deviation is shown. For Northerns, the signal intensity was measured with a phosphorimager after overnight exposure. Each concentration spot (solid square) represents the mean of two different experiments.

FIG. 3A depicts an analysis of total RNA from fresh and FFPE anaplastic oligodendroglioma tissue on 1% agarose gels. Ribosomal RNAs (28S and 18S) are indicated. FIG. 3B depicts an analysis of low molecular weight RNA from fresh and FFPE anaplastic oligodendroglioma tissue on 3% agarose gels. "T"=total RNA; "L"=larger RNA only, and "S"=low molecular weight RNA, used for the RAKE assay. The lanes labeled "FFPE" (tumor sample), represent ⅕th of the RNA isolated from a single 50 micron-thick section (approximately 1 μg of RNA).

FIG. 5 shows the profiling and relative abundance of different miRNAs using RAKE. H=HeLa; J=Jurkat; M=malignant meningioma; PO=FFPE tissue from anaplastic oligodendroglioma; FO=Fresh tissue from anaplastic oligodendroglioma. Light gray squares represent no signal, black squares represent low signal, and cross-hatched squares represent highest signal.

FIG. 6A shows a comparison between different biological replicates in Jurkat cells ($R^2$>0.9). FIG. 6B shows a comparison between Jurkat cells and fresh anaplastic oligodendroglioma tissue. Notably, in contrasting FIG. 6A with 6B, there is poor correlation in the expression levels of miRNAs between the two samples, ($R^2$=<0.2), yet many miRNAs are highly expressed in both tissues. FIG. 6C shows a comparison between RAKE signals from anaplastic oligodendroglioma RNA isolated from FFPE or from fresh material ($R^2$>0.9).

FIGS. 8A thru 8D demonstrate that RAKE is superior to Northern blots in discriminating between miRNA paralogs. FIG. 8A provides nucleic acid sequences (SEQ ID Nos:1, 2 and 4-7) of the three pairs of paralogous miRNAs tested. 0.1 pmoles ($6\times10^{10}$ molecules) of each synthetic, paralogous miRNA was analyzed by RAKE or Northern blots. Representative experiments for the hsa-miR-23a/23b pair, SEQID Nos:1 and 2, respectively, are shown in FIGS. 8B and 8C for RAKE and Northerns, respectively. In FIG. 8D, the mean signal intensity for each miRNA was determined using RAKE (n=12) and Northern blots (n=2), and a ratio between the paralogous miRNAs was calculated for each pair, as indicated.

DETAILED DESCRIPTION OF CERTAIN EMBODIMENTS OF THE INVENTION

Figure 1:
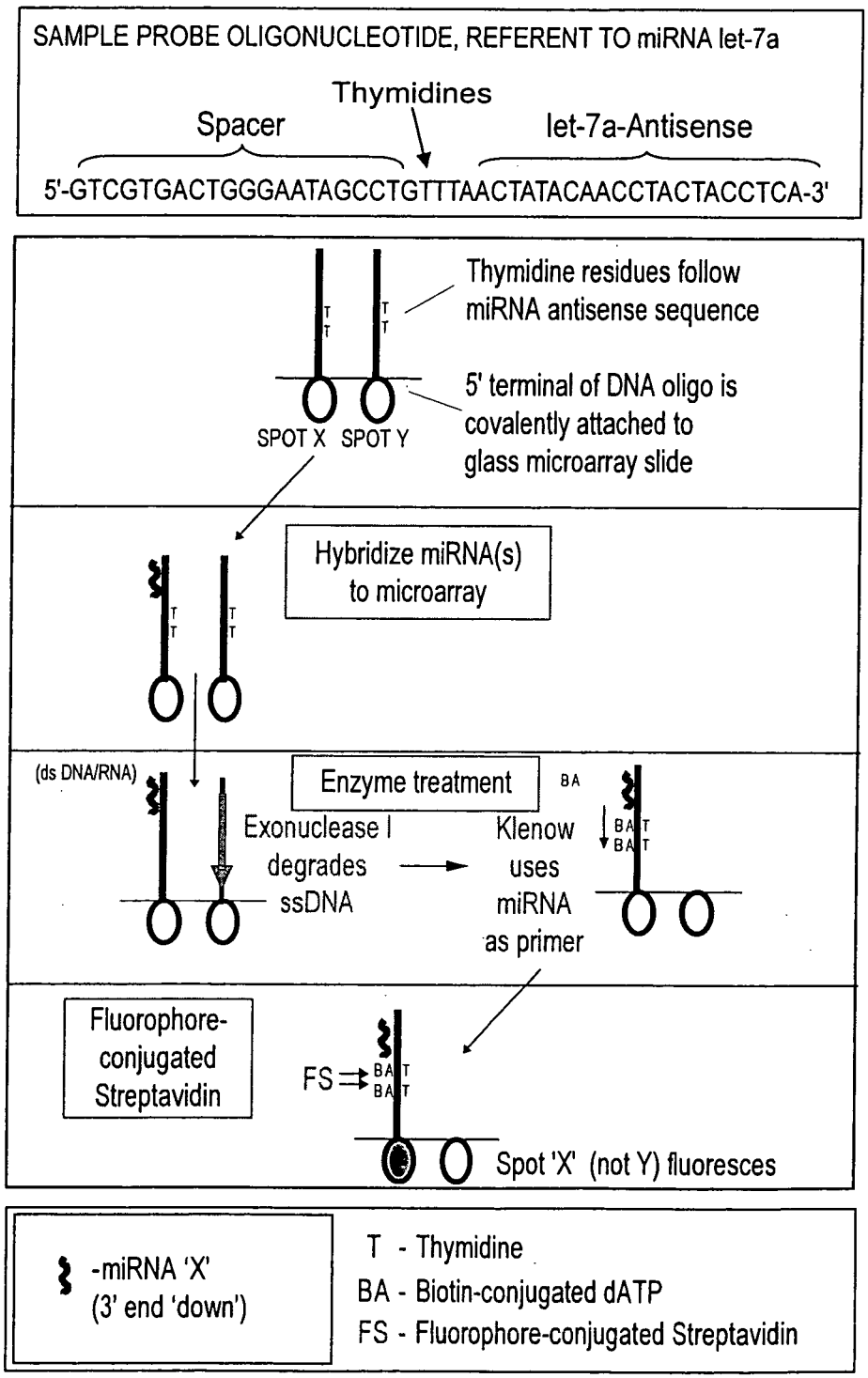
FIG. 1 is a schematic diagram of the RNA-primed, Array-based, Klenow Enzyme (RAKE) assay. The sample probe (SEQ ID No:3) at the top of the figure illustrates the generic structure of the DNA oligonucleotides used on the microarray. The nucleotides at the 5' side comprise a spacer, which is constant for all the probes, followed by three thymidine nucleotides. The variable portion of each probe is at the 3' end, which is the antisense sequence of various miRNAs.

The present invention provides DNA microarray techniques that allow hybridization of nucleic acids without RNA amplification, without using cDNA, and without labeling the nucleic acid prior to hybridization. The term "nucleic acid" as used herein, may include any polymer or oligomer of pyrimidine and purine bases, preferably cytosine, thymine, and uracil, and adenine and guanine, respectively. See Lehninger, *Principles Of Biochemistry*, at 793-800 (Worth Pub. 1982).

"Nucleic acid" refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs.

Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "nucleic acid library" or sometimes "array" as used herein, refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate.

The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "hybridization" as used herein, refers to the process in which two single-stranded polynucleotides bind noncovalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization."

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook et al., *Molecular Cloning A laboratory Manual*, 2nd Ed., Cold Spring Harbor Press (1989), herein incorporated by reference in its entirety.

The term "hybridization conditions" as used herein will typically include salt concentrations of less than about 1M, usually less than about 500 mM, and preferably less than about 200 mM. When the term "effective amount" is used herein, it refers to an amount sufficient to induce a desired result. Hybridization temperatures can be as low as 5° C., but are typically >22° C., more typically >30° C., and preferably >37° C. Longer sequence fragments may require higher hybridization temperatures for specific hybridization. Other factors may affect the stringency of hybridization, including base composition and length of the complementary strands, presence of organic solvents and extent of base mismatching, as a result the combination of parameters is more important than the absolute measure of any one alone.

The term "hybridization probe" as used herein, refers to an oligonucleotide capable of binding in a base-specific manner to a complementary strand of nucleic acid. Such probes include peptide nucleic acids, as described in Nielsen et al., *Science* 254, 1497-1500 (1991), and other nucleic acid analogs and nucleic acid mimetics. The term "hybridizing specifically to" as used herein, refers to the binding, duplexing, or hybridizing of a molecule only to a particular nucleotide sequence or sequences under stringent conditions when that sequence is present in a complex mixture (for example, total cellular) DNA or RNA.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as, on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "probe to-target pair" is formed when two macromolecules have combined through molecular recognition to form a complex (also referred to in the art a receptor-to-ligand binding).

The term "complementary" as used herein, refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%.

Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, e.g., Kanehisa, *Nucleic Acids Res.* 12:203 (1984), incorporated herein by reference.

The microarray assay process is referred to herein as a Double-stranded Exonuclease Protection (DEP) assay. The term "array" as used herein, refers to an intentionally created collection of molecules which can be prepared either synthetically or biosynthetically. The molecules in the array can be identical or different from each other. The array can assume a variety of formats, such as for example, libraries of soluble molecules; libraries of compounds tethered to resin beads, silica chips, or other solid supports. The term "solid support," "support," and "substrate" as used herein, are used interchangeably and refer to a material or group of materials having a rigid or semi-rigid surface or surfaces. In the exemplified embodiment the substrate is a glass slide. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See, e.g., U.S. Pat. No. 5,744,305 for other exemplary substrates.

DEP employs DNA oligonucleotides ("oligomers") for spotting on glass-slides to establish the microarrays. The DNA oligonucleotides (referred to simply as an "oligonucleotide" or "oligomers") as used herein, means a nucleic acid ranging from at least 2, preferable at least 8, and more preferably at least 10-15, and more preferably at least 20-30 nucleotides in length, or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing, such as Hoogsteen base pairing, which has been identified in certain tRNA molecules and are postulated to exist in a triple helix. "Polynucleotide" and "oligonucleotide" are used interchangeably in this application.

The oligonucleotides used in the present invention can be individually prepared by one of ordinary skill in the art, or they may be purchased, since many are commercially-available. In the present invention, the preferred oligonucleotides include biotinylated thymidine residues.

The term "monomer" as used herein, refers to any member of the set of molecules that can be joined together to form an oligomer or polymer. The set of monomers useful in the present invention includes, but is not restricted to, for example, (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basic sets of monomers may be used at successive steps in the synthesis of a polymer. The term "monomer" also refers to a chemical subunit that can be combined with a different chemical subunit to form a compound larger than either subunit alone.

The term "isolated nucleic acid" as used herein, mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods). The term "mixed population" or "complex population" as used herein, refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population, but also include other undesirable populations. For example, a complex population of nucleic acids may be a sample which has been enriched for desired messenger RNA (mRNA) sequences, but still includes some undesired ribosomal RNA sequences (rRNA). The oligonucleotide spots are preferably isolated nucleic acids.

The term "primer" as used herein, refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

In practice, each spot on the microarray slide contains one oligonucleotide arranged in the following orientation:

| | constant portion | | varying portion | |
|---|---|---|---|---|
| Slide - - - | 5' end-m13 - - - | (spacer 20 nucleotides) | - - - biotinylated thymidine | - - - antisense sequence-3' |

The present microarray-based technique is effective on any single-stranded (ss) molecule, including single-stranded DNA or RNA, but collectively is referred to herein as an "RNA sample," specifically including mRNAs. The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc, are all derived from the mRNA transcript, and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

As the term RNA is used herein, it is further intended that the term also encompasses other single-stranded nucleic acids, including ss-DNA. Likewise, although the process referred to is RNA expression profiling, it is further intended to include other single-stranded nucleic acids, including ss-DNA.

When the microarray assay is used for RNA expression profiling in accordance with the present invention, the hybridization solution is applied to the slide without prior amplification or labeling. Hybridization occurs in standard hybridization buffers and conditions. During incubation of the hybridization treated slide, the RNA hybridizing to the antisense portion (3' portion) of the oligonucleotide will produce a double-stranded DNA-RNA hybrid (or series of short double-stranded DNA-RNA hybrids). By comparison, spots that contain single-stranded antisense DNA oligonucleotides are not hybridized, thus those oligonucleotides remain single-stranded.

Following hybridization, the slide is washed. Then, using a buffer solution that has been modified slightly from the commercial recommendations, the slide is incubated overnight with Exonuclease I (New England Biolabs). Exonuclease I catalyzes the hydrolysis of single-stranded DNA oligonucleotides to form free nucleotide residues. Hence for the (non-hybridized) single-stranded oligonucleotide-containing microarray spots, the biotinylated thymidine residue will be cut away from the microarray, whereas the (hybridized) double-stranded oligonucleotide:RNA-containing microarray spots continue to include the biotinylated thymidine residue (i.e., the exonuclease digests the single-stranded-DNA oligonucleotide).

Following incubation with Exonuclease I, the slides are again washed, and then incubated for 30 minutes at room temperature with a solution containing streptavidin-conjugated Alexa fluor dye (SCAF) (Molecular Probes). The SCAF binds avidly to the biotinylated residues in the microarray-bound oligonucleotides. As a result, SCAF only binds to those oligonucleotides that bound to the RNA sample (i.e., those that were protected from the single-stranded-DNA-specific Exonuclease I). Consequently, in the DEP assay, only the SCAF-bound oligonucleotide spots are fluorescent when the slide is evaluated by the detection device, e.g., the slide scanner machine.

Of course, Exonuclease I is used only as an example of an effective exonuclease in the DEP assay. In fact, any exonuclease that effectively catalyzes hydrolysis of non-hybridized single-stranded oligonucleotides in the spot to form free nucleotide residues, may be used provided that they (1) satisfy the basic criteria of strictly catalyzing 3'→5'-directed nucleotide hydrolysis; (2) are independent of nucleotide identity; and (3) work under conditions in which stable DNA/RNA hybrids are retained.

SCAF is also used only as an example of an effective marker. Other streptavidin-conjugated fluorophores or other luminescent labels may also be used, so long as the labeling method is combined with the essential step of using the double-stranded DNA/hybridized RNA as a protection assay in the presence of an exonuclease. This preserves a residue that can be labeled by the fluorophore or other luminescent label. In general, the term "label" as used herein refers to a luminescent label, a light scattering label or a radioactive label. Fluorescent labels include, inter alia, the commercially available fluorescein phosphoramidites, such as, Fluoreprime (Pharmacia), Fluoredite (Millipore) and FAM (ABI). See also U.S. Pat. No. 6,287,778.

Furthermore, in an alternative embodiment, the present technique could be augmented by co-hybridization with a probe that recognizes the spacer portion of the oligonucleotide. Such a probe would employ a fluorescent or luminescent marker that is different from SCAF, i.e., red vs. green, to allow for a rigorous normalization of the amount of oligonucleotide DNA present in each spot. It also allows for good compensation for spot-to-spot heterogeneity.

The term "probe" as used herein refers to a surface-immobilized molecule that can be recognized by a particular target. See, e.g., U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

As previously noted, the Northern blot is considered the standard method for miRNA validation and quantification (Ambros et al., 2003). The Northerns are theoretically straightforward and their use has been well-established in biomedical research. Northern blots offer both quantitative and qualitative information, and unlike a microarray experiment, a Northern blot confirms the length of the hybridized transcripts. The Northern blots are, however, laborious, making them less useful or well-suited for high-throughput expression profiling.

Accordingly, the present invention further provides a microarray platform that enables high-throughput gene expression analyses of small RNAs. Termed the RNA-primed Array-based Klenow Enzyme (RAKE) assay, this embodiment of the invention provides a new tool with high sensitivity and specificity for miRNA profiling.

Figure 7:
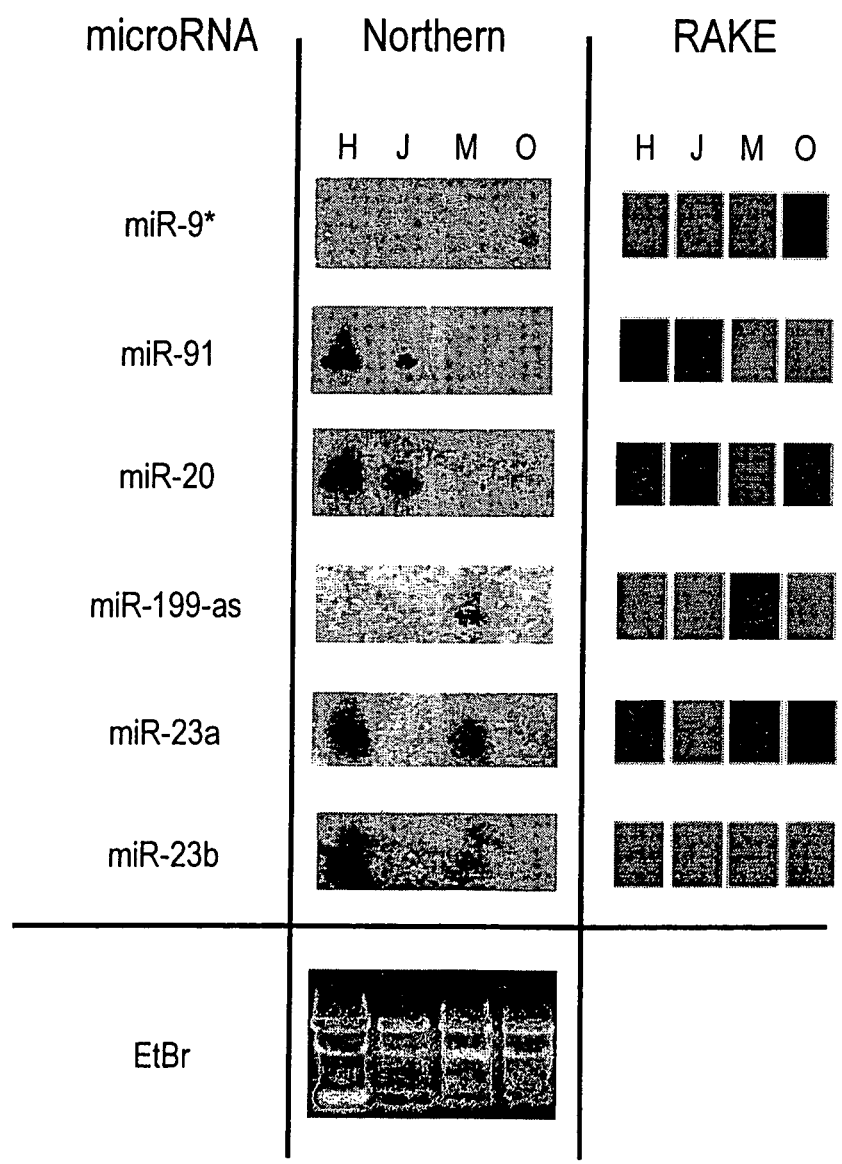
FIG. 7 depicts the correlation between Northern blots and RAKE assays for HeLa (H), Jurkat (J), malignant meningioma (M), and anaplastic oligodendroglioma (0), 5 μg total RNA loaded per lane. The quality of the total RNA is assessed by electrophoresis on 1% Agarose gels, followed by ethidium bromide (EtBr) staining (a representative gel is shown as an insert at the bottom of FIG. 7). Northern blots are shown on the left; corresponding RAKE assay results are shown on the right.

By comparison, the present RAKE assay is quite simple, involving minimal steps, and it is particularly suited for high-throughput expression profiling. The RAKE assay also provides unique qualitative data, because the 3' end of the miRNA "primer" hybridizes specifically to the oligonucleotide "template." As a result, RAKE appears to be superior to Northern blots in discriminating the exact 3' end of the sample miRNAs, offering a significant advantage because for many mature miRNAs, the paralogs differ at the 3' end. These miRNAs, derived from different genes, would be expected to cross-react adversely in Northern blots (and in standard microarray methods using labeled target pools), but such adverse reactions do not usually occur in the RAKE assay. As shown in FIGS. 7 and 8, data from hsa-miR-23a/23b (SEQ ID Nos: 1 and 2, respectively) and two other pairs of paralogous miRNAs, support the hypothesis that the RAKE assay is superior to Northern blots for discriminating miRNA paralogs.

Advantageously, RAKE requires no sample RNA manipulation. Possible biases, which may be introduced during enzymatic labeling, or cDNA generation or amplification of the sample RNA prior to hybridization to the glass microarray, are thus avoided. Thus RAKE allows for rapid and simultaneous detection of all known miRNAs from the same sample. Moreover, RAKE advantageously permits the complete automation of all steps—from sample hybridization to detection. This is achieved by using a number of existing technologies and equipment, previously used for traditional mRNA microarrays, and allows for highly consistent performance.

RAKE involves the generation of microarray-containing spotted oligonucleotides, wherein each DNA oligonucleotide is oriented on the slide essentially as set forth above for the DEP assay. The "constant portion" directly adjacent to the slide is the 5' end of m13(spacer 20 nucleotides) including thymidine residues, next to that is the "variable portion" comprising the antisense sequence-3'.

The RAKE technique involves a two-stage reaction. First, the microarray is incubated along with Klenow enzyme, enzyme buffer (containing $Mg^{++}$), conjugated dATPs (for labeling), and an RNA sample. Some of the RNA sample hybridizes to the "antisense" (3') sequence of the DNA oligonucleotide. Sequences that bind tightly, and are hybridized at the 3' end, can act as primers for the Klenow DNA polymerase (it has been demonstrated that Klenow enzyme can act as a RNA-primer-directed DNA polymerase). In the present case, the Klenow fragment of DNA polymerase I is applied to catalyze the addition of biotin-conjugated dNTPs, such as dATPs, using the miRNA as a primer and the spotted probe as template. Since the incorporation of dideoxyNTPs (ddNTP) rather than dNTP is a random event, the reaction will produce DNA fragments varying in length. In a preferred embodiment, the ratio of dNTP to ddNTP is selected to generate DNA fragments of a predetermined size range. For example, DNA fragments sized may range from 20 to 50, 35-75, or 50 to 200 bases. Hence, the dATPs that can be labeled, only hybridize to oligonucleotide "spots" on the microarray that are antisense to RNAs present in the sample.

Technical 'tweaks' could greatly enhance/broaden the potential applications for RAKE. For example, longer RNAs including mRNAs (for transcript splice variant profiling) may be assessed in the microarray assay using a nuclease that cleaves non-hybridized RNA. The potential applications for these techniques are very broad, but include expression analyses of microRNAs (any species), siRNAs (experimentally introduced or endogenous), and other small regulatory RNAs. Other potential RNA applications include profiling and quantification of viruses, as well as other RNA profiling.

Moreover, RAKE could be made a great deal more sensitive as needed, by utilizing one of various "sandwich" or signal amplification techniques (e.g., streptavidin HRP, biotin antibodies, chemiluminescence, etc). This is analogous to the discussion regarding the DEP assay above.

The present invention utilizes glass slide substrates for the microarrays, e.g., CodeLink glass slides, with amine-modified DNA oligonucleotide probes spotted robotically, and specifically immobilized via attachment at the 5' end (described in greater detail in the Example that follows). This technique provided results that on a technical level, proved to be consistent with findings in prior microarray experiments. For RNA targets analyzed using DNA oligonucleotide probe-based microarrays, the probe-to-target cross-hybridization is seen only if the degree of theoretical cross-hybridization is >80% for 50-70 mer probes (Dai et al., *Nucleic Acids Res.* 30:e86 (2002)), and 90% or more for an ~20 mer probe, depending upon variables that include hybridization conditions, probe G/C composition, and the location of the 'mismatched' nucleotide(s) (Ramakrishnan et al., *Nucleic et al., Appl. Acids Res.* 30:e30 (2002); El Fantroussi, *Environ. Microbiol.* 69:2377-2382 (2003); Koizumi et al., *Appl. Environ. Microbiol.* 68:3215-3225 (2002); Liu et al., *Environ. Microbiol.* 3:619-629 (2001); Dorris et al., BMC Biotechnol. 3:6 (2003)), CodeLink slide microarrays have been shown to demonstrate excellent hybridization characteristics (Ramakrishnan et al., 2002; Dorris et al., 2003).

The RAKE assay was devised to exploit the known ability of the Klenow enzyme fragment to act as a DNA polymerase using an RNA primer on a DNA oligonucleotide template (Huang et al., *Nucleic Acids Res.* 24:4360-4361 (1996); Huang et al., *Anal. Biochem.* 322:269-274 (2003)). Prior studies have demonstrated on-slide enzymatic reactions and primer extension (see, e.g., Nikiforov et al., *Nucleic Acids Res.* 22:4167-4175 (1994); Head et al., *Nucleic Acids Res.* 25:5065-5071 (1997)). However, direct detection of RNA hybridization (using RNA-primed DNA polymerase) has not been reported on a microarray, nor have the special properties of the Klenow enzyme been used on such microarray studies.

It was also necessary to use Exonuclease I, a 3'→5', single-stranded, DNA-specific exonuclease, which is highly processive (Brody et al., *J. Biol. Chem.* 261:7136-7143 (1986)). It is important to note that the activities of both Klenow enzyme and exonuclease (Brody et al., 1986) are independent of the sequence of their substrates. Systematic bias is, therefore, not introduced, and the results produced by the present invention demonstrate sensitivity to the level of 10 picograms (pg) of target miRNA, which is comparable to Northern blots Lim et al., 2003. In contrast, however, RNA ligases are prone to bias because enzyme kinetics change with substrate sequence (see Ohtsuka et al., 1977, supra; Romaniuk et al., 1982, supra), producing an inaccurate representation of the miRNAs present in a target pool labeled by RNA ligase methods.

In alternative embodiments of the present invention, even greater sensitivity may be obtained using 'sandwich'-type amplification, or a more sensitive labeling technique (e.g., gold particles for Resonance Light Scattering). Quantification of miRNA abundance, and resolution of expression differences, may be improved by incorporating a standard reference that hybridizes to the spacer sequence and is detected with a second scanner channel.

The results provided by the present invention have proven to be broadly compatible with those produced using Northern blots, e.g., Sempere et al., (2004, supra), although the present methods are far more efficient and effective. In each sampled tissue, only a minority of miRNAs are expressed at detectable levels a given time in a given tissue.

Some miRNAs appear to be widely expressed, including miR-98, let-7 paralogs, miR-16, miR-26a, and miR-100. MiR-124a and miR-9, which were found only in samples from anaplastic oligodendrogliomas, are reportedly highly restricted, being expressed only in the central nervous system (Sempere et al., 2004, supra; Lim et al., 2003, supra). MiR-92, which is present in cultured cells, but not appreciably in the sampled tissues (Sempere et al., 2004), is also present in HeLa cells and Jurkat cells, but not in the tested primary tumor tissue described in the Example that follows. Finally, there is general agreement between the HeLa expression profile set forth herein as a result of the RAKE analysis, and the miRNAs evaluated previously in HeLa cells (Lagos-Quintana et al., 2001, supra; Mourelatos et al., *Genes Dev.* 16:720-728 (2002)). In the Example that follows, there was also the surprising finding that miR-20 showed stronger expression than one may have expected from prior studies. This expression was validated by Northern blot (FIG. 7).

Jurkat cells are derived from a T cell lymphoma (Gillis et al., *J. Exp. Med.* 152:1709-1719 (1980)). In prior studies of chronic B cell lymphomas, miR-15a and miR-16 were deleted or down-regulated in more than two thirds of cases (Calin et al., 2002, supra), whereas miR-155 was highly expressed in Burkitt lymphoma (Metzler et al., *Genes Chromosomes Cancer* 39:167-169 (2004)). By contrast, Jurkat cells show strong expression of both miR-15a and miR-16, and low expression of miR-155.

The sensitivity of the RAKE assay provides for sensitive, specific and high-throughput miRNA expression profiling, consistently produced robust signals at 0.16 fmoles, equal to about $10^8$ molecules of miRNA. However, in contrast to the microarrays developed, e.g., by Liu et al., 2004, supra, and Miska et al., 2004, supra, the RAKE assay does not require or involve the generation of a cDNA library, nor is amplification of the RNA sample necessary. In fact, the RAKE assay avoids sample RNA manipulation altogether. Moreover, the RAKE assay appears to be superior to prior art methods for discriminating paralogous miRNAs that differ at their 3'-ends, since the prior art techniques rely solely on hybridization to detect and discriminate between miRNA paralogs.

In addition, since blocks of formalin-fixed and paraffin-embedded (FFPE) tissue can be assessed using the RAKE technique (or other miRNA tools) as described in greater detail in the Example that follows, the present invention permits samples to be analyzed from the voluminous archive of human pathological specimens. This will provide a better understanding of the roles of miRNAs in healthy and disease conditions.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference.

The present invention also contemplates many uses for oligomers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example, Setubal et al., *Introduction to Computational Biology Methods* (PWS Publishing Company, Boston, 1997); Salzberg, Searles, Kasif, (Ed.); *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis, *Bioinformatics: A Practical Guide for Analysis of Gene and Proteins* (Wiley & Sons, Inc., $2^{nd}$ ed., 2001). See also, e.g., U.S. Pat. No. 6,420,108.

The present invention may also make use of various computer program products and software for a variety of purposes, such as probe design, management of data, analysis, and instrument operation. See, e.g., U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621, 10/063,559, 10/065,856, 10/065,868, 10/328,818, 10/328,872, 10/423,403, and 60/482,389.

Additional objects, advantages and novel features of the invention will be set forth in part in the detailed protocols used as non-limiting examples that follow, and in part will become apparent to those skilled in the art on examination of the following, or may be learned by practice of the invention. The following examples, however, are understood to be illustrative only and are not to be construed as limiting the scope of the appended claims.

EXAMPLES

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV); *Using Antibodies: A Laboratory Manual*; *Cells: A Laboratory Manual*; *PCR Primer: A Laboratory Manual*; and *Molecular Cloning: A Laboratory Manual* (all from Cold Spring Harbor Laboratory Press), Stryer, (1995) *Biochemistry* (4th Ed.) Freeman, N.Y.; Gait, "Oligonucleotide Synthesis: A Practical Approach" 1984, IRL Press, London; Nelson and Cox (2000); Lehninger, *Principles of Biochemistry* 3rd Ed., W.H. Freeman Pub., New York, N.Y.; and Berg et al. (2002) *Biochemistry*, 5th Ed., W.H. Freeman Pub., New York, N.Y., all of which are herein incorporated in their entirety by reference for all purposes.

Methods for conducting polynucleotide hybridization assays have been well developed in the art. Hybridization assay procedures and conditions will vary depending on the application and are selected in accordance with the general binding methods known including those referred to in: Maniatis et al., *Molecular Cloning: A Laboratory Manual* ($2^{nd}$ Ed. Cold Spring Harbor, N.Y, 1989); Berger and Kimmel, *Methods in Enzymology*, Vol. 152, *Guide to Molecular Cloning Techniques* (Academic Press, Inc., San Diego, Calif., 1987); Young and Davis, *P.N.A.S*, 80: 1194 (1983). Methods and apparatus for carrying out repeated and controlled hybridization reactions have also been described in U.S. Pat.

Nos. 5,871,928, 5,874,219, 6,045,996 and 6,386,749, 6,391,623 each of which are incorporated herein by reference.

The present invention also contemplates signal detection of hybridization between ligands in certain preferred embodiments. See, e.g., U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194, 60/493,495 and in PCT Application PCT/US99/06097 (published as WO99/47964), each of which also is hereby incorporated by reference.

RNA Isolation and Northern Blots.

Cell batches (from HeLa and Jurkat cells) and RNA were processed separately for biological replicates. RNA was purified initially using Trizol™ LS reagent (InVitrogen, Carlsbad, Calif.). Human tissue was procured in accordance with accepted procedures. From archival FFPE tissue blocks, RNA was initially isolated essentially as previously described (Korbler et al., *Exp. Mol. Pathol.* 74:336-340 (2003)). Briefly, Citrisolv™ (Fisher Scientific, Pittsburgh, Pa.) was used as a xylene substitute, and Trizol™ LS was used after deparaffinization. CitriSolv™ clearing/deparaffinizing agent, is non-toxic and biodegradable, and provided results comparable with xylene.

Fresh tissues from two different brain tumors (a malignant meningioma and an anaplastic oligodendroglioma) were dissected by a neuropathologist. Fresh tissue was placed in a RNALater™ solution (Ambion, Inc, Austin, Tex.). RNA was subsequently isolated from this fresh tissue using Trizol™. For the anaplastic oligodendroglioma, the RNA from fresh tissue was compared against adjacent tissue from the same tumor that had been formalin-fixed and paraffin-embedded (FFPE) using conventional anatomic pathology methods. For fresh tissue, cultured cells, and FFPE tissue, RNA was further processed using a kit designed to isolate low molecular weight RNA (MirVana™ kit from Ambion). For Northern blots, whole RNA was isolated from the cells or tissues using the Trizol™ LS reagent. RNA was then run on 20% urea-PAGE gels, blotted, and probed using 5'-end radiolabeled probes against the indicated miRNAs, as previously described by Nelson et al., *RNA* 10:387-394 (2004)). Blots were exposed on phosphorimager screens overnight and signals were scanned and quantified using a Storm 860 Phosphorimager (Molecular Dynamics, Sunnyvale, Calif.).

Microarray Platform.

Probe DNA oligonucleotides were synthesized at 600 pmol on 384-well plates (Qiagen), each containing a 5' terminal C6-amino modified linker. Each probe had a sequence as depicted in FIG. 1 (5'linker, m13-like 'spacer', thymidines, and sequence antisense to miRNAs), except for a control probe, which contained the spacer only. Probes were suspended at 40 µM in 150 mM sodium phosphate buffer (pH 8.5; 200U/ml print buffer) with 0.0005% Sarkosyl.

A GeneMachines OmniGrid 100™ robot printed probes onto CodeLink™ slides (Amersham Bioscience, Piscataway, N.J.) at 30-35% humidity at 24-27° C. Each spot element measured 120 µm in diameter with center-to-center spacing of 400 µm. Each glass slide contained 6 spots (three spatially separated pairs) corresponding to each probe, for a total 1422 spots including controls. Further chemical 'blocking' of the spotted glass slide was found to be unnecessary.

RAKE Protocol.

Small RNA hybridizations were found to optimally include more than 2 µg total mass per slide. Less can be used, but the signal was weaker for less-abundant miRNAs. Spotted microarray slides were processed using an automated hybridization apparatus (Tecan HS4800, Tecan Trading AG, Switzerland), which greatly facilitated sample processing and allowed near-identical handling of all microarray slides throughout.

The concentrated hybridization buffer is composed of 15% formamide, 15×SSC. DNA oligonucleotide spike-ins corresponding to plant (*Arabidopsis thaliana*) miRNAs ath-miR-157, ath-miR-163, and ath-miR-169 prepared beforehand in a solution at $10^{-7}$ M, $10^{-8}$ M, and $10^{-9}$ M, respectively, diluted in water. For all hybridization and enzymatic steps, RNAsin (0.4U/µl; Promega Biosciences, Inc., San Luis Obispo, Calif.) was included. The protocol involves the following sequence: 1 minute wash in 2×SSC at 25° C.; 5 minute rinse in 5×SSC with 10% formamide at 25° C.; 3×30 second rinses in 2×SSC at 25° C.; 18 hour target/probe hybridization (35 µl concentrated hybridization buffer, 65 µl small RNA preparation containing 4 µg low molecular weight RNA, and 10 µl plant DNA spike-in solution, which were together heated to 75° C. and allowed to cool at room temperature prior to hybridization) at 25° C. This was followed by 3×1 minute rinses in 2×SSC at 37° C.; 3 hour incubation with Exonuclease I (New England Biolabs, Ipswich, Mass.; fresh buffer at pH 7.5; 4U/pi) at 27° C.; 3×1 min. rinses in 2×SSC at 27° C.; 10 minute rinse in 2×SSC with 0.05% SDS at 27° C.; 4×1 minute rinse in 2×SSC at 37° C.; 60 minute incubation with Exo(−) Klenow (Promega; 0.15 U/µl) in 1×DNA polymerase buffer (Promega) with biotin-7-dATP (InVitrogen; 4 µM) at 27° C.; 2×1 min. rinse in 2×SSC at 25° C.; 30 min incubation with streptavidin-conjugated Alexa-fluor-547 (Molecular Probes; 15 ng/µl) at 25° C.; 3×1 min. rinses in 2×SSC at 25° C.

Validation Steps.

A concentration curve was generated using a synthetic target RNA oligonucleotide (miR-124a) in the background of a complex RNA mixture (low molecular weight RNA isolated from HeLa cells, a cell line that does not contain miR124a). Plant miRNA spike-ins were used at concentrations listed above.

For validating Northern blots, all of the miRNAs that were tested are set forth in FIG. 7.

Image Analysis and Data Processing.

Slides were scanned using a Genepix 4000B laser scanner (Axon, Molecular Devices, Sunnyvale, Calif.) at a constant power level and sensitivity (550 PMT) using a single color channel (532 nm wavelength). Non-hybridizing and artifact-associated spots were eliminated by both visual- and software-guided flags. Image intensities were measured as a function of the median of foreground minus background. Negative values were normalized to zero, but no other normalizations were performed. Images were analyzed using the Genepix Pro5.0 software package. Excel and Genespring 6.2 were used for further data analysis. Testing discrimination of miRNA paralogs.

RNA oligonucleotides corresponding to 3 different miRNA paralogous pairs (6 different miRNAs; FIG. 8A) were synthesized and purified by PAGE. Corresponding antisense DNA oligonucleotides were also made, and served as probes in Northern blots. RAKE experiments were performed using 0.1 pmoles (~$6 \times 10^{10}$ molecules) of each synthetic miRNA.

Hybridizations were performed in a complex mixture containing 2 µg of small RNA from Jurkat cells (which do not normally express any of these 6 synthetic miRNAs; see FIG. 5). Microarray experiments contained 6 spots (probes) for each synthetic miRNA and were performed in duplicate (12 spots total for each synthetic miRNA). 0.1 pmoles of each synthetic miRNA was fractionated on 15% urea-PAGE for Northern blots, which were performed in duplicate. Detection and signal quantification for RAKE assays and Northern blots were performed as described above.

Assay Development and Validation.

A method was developed to achieve high-throughput gene expression analyses of miRNAs. To eliminate systematic bias associated with RNA ligation steps, amplification/cDNA intermediaries, or separate fluorophore labeling, on-slide enzymatic reactions, methods recognized in the art for other purposes, were used.

The assay is shown in schematic form in FIG. 1. DNA oligonucleotide probes, having 3'-halves complementary to specific miRNAs (e.g., let-7a) and having shared 5'-halves (spacer), were synthesized and covalently cross-linked at their 5' termini onto glass microarray slides. Three thymidines separated the spacer from the remainder of the DNA probe, which was antisense to specific miRNAs. The RNA sample, containing miRNAs, was hybridized and after washes the slide was treated with Exonuclease I, which specifically degraded single stranded, unhybridized, probes. The slide was again washed and the Klenow fragment of the DNA polymerase I was applied along with biotinylated dATP (B-dATP). While any biotin-conjugated dATP may be used, and it is available in many places, in the present example, biotin-7-dATP (InVitrogen) was used. The hybridized miRNAs act as primers for the Klenow enzyme and the immobilized DNA probe acts as a template, leading to incorporation of B-dATPs. The slide was then washed and a streptavidin-conjugated fluorophore was applied to visualize and analyze the spots containing hybridized and Klenow-extended miRNAs.

In principle, either the Exonuclease I reaction (protection of a tagged, immobilized probe from nuclease by hybridization to a miRNA) or the Klenow DNA polymerase (primer extension from the hybridized miRNA on an immobilized probe template) should be effective alone to produce accurate microarray-based detection of miRNAs. However, microarrays and protocols designed to use either of these enzymes without the other, resulted in high background signal levels. It was subsequently determined that the sequential application of these enzymes, as described above (FIG. 1 and below) was optimal. A glass slide microarray was developed, including probe spots corresponding to 239 miRNAs (sequences were obtained from the official microRNA registry (Griffiths-Jones, *Nucleic Acids Res.* 32 Database issue, D109-111 (2004)) spotted in three pairs throughout the slide for a total of 1422 spots per microarray, including miRNAs from humans, mice, rats, and *Arabidopsis thaliana*.

Included also were DNA probes complementary to plant miRNAs on the microarray, both for negative controls and for future studies involving *Arabidopsis thaliana*. Three separate *Arabidopsis* miRNA spike ins were used. Synthetic DNA oligonucleotides corresponding to the three plant miRNAs (ath-miR-157, ath-miR-163, and ath-miR-169) were introduced in each hybridization step. For each hybridization, the final concentration of ath-miR-157, ath-miR-163, and ath-miR-169 were $10^{-9}$ M, $10^{-10}$ M, and $10^{-11}$ M, respectively. These spike-in DNA oligonucleotides were used to assist normalization, and to provide absolute reference points for each study (see below and FIG. 2). AthmiR-157, at $10^{-9}$ M ($6.02 \times 10^{10}$ probe molecules/100 µl hybridization reaction), provided an internal control for the highest fluorescent signal level.

The sensitivity of the RAKE assay was investigated by using a synthetic RNA target oligonucleotide corresponding to the sequence of mature miR-124a. The results are shown in FIG. 2A, with each concentration representing duplicate arrays (12 data points each). Low molecular weight (LMW) RNA isolated from HeLa cells was included to compose a complex RNA background. MiR-21 (a normal component of HeLa cells) and the miR-157 DNA spike-in did not vary significantly at different concentrations of miR-124a (FIG. 2A). The dynamic signal of miR-124a spanned at least three orders of magnitude (FIG. 2A). These results were not normalized, and thus demonstrate the robust nature of the raw data.

The technique is comparably sensitive to Northern blots (FIG. 2B), allowing detection of miRNA in the <10 pg range, which is consistent with prior studies using Northern blots on miRNAs. The microarray data shows slightly less sensitivity, some variability at very low concentrations, and slightly less linearity across the large scale of concentrations when evaluated (five orders of magnitude), in comparison to Northern blots (FIG. 2C). These differences are due to different saturation profiles inherent to microarray fluorescence, as compared with radiation detection.

RNA Isolation and Processing for RAKE.

RNAs derived from human epithelial and hematopoietic cell lines were evaluated, as well as RNAs derived from two human brain tumors (Table 1).

TABLE 1

Summary of tissues used in RNA studies.

| Cells/Tissue Designation | Tissue Types | Amount of cells or tissue needed |
| --- | --- | --- |
| HeLa | Human epithelial cancer cell line | $10^6$ cells |
| Jurkat | Human T-cell derived lymphoma cell line | $10^6$ cells |
| Malignant Meningioma | Fresh human brain tumor | <500 µg |
| Anaplastic oligodendroglioma (AO-Fresh) | Fresh human brain tumor | <500 µg |
| AO-FFPE | Same tissues as above, formalin-fixed, paraffin embedded | 1-4. 50 µm thick sections |

For HeLa cells, see Hsu, *Tex. Rep. Biol. Med.* 12: 833-846 (1954); Scherer et al., *J. Exp. Med.* 97: 695-710 (1953).
For Jurkat cells, see Gillis et al., *J. Exp. Med.* 152: 1709-1719 (1980).
For Anaplastic oligodendroglioma (AO-Fresh), tissue was adjacent to AO-P section.

Figure 3:
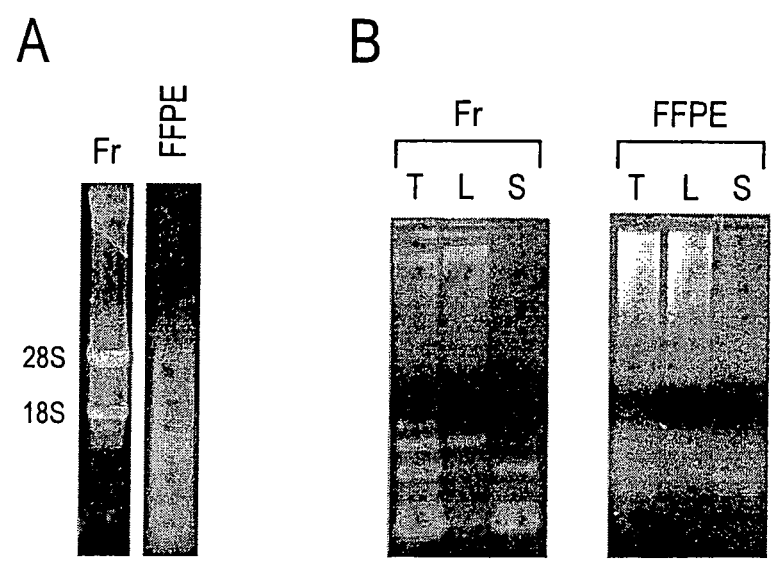
FIGS. 3A and 3B are photographic images of representative agarose gels used to characterize the RNA used in the RAKE assay. "Fr" represents RNA from fresh brain tumor, whereas "FFPE" represents RNA from formalin-fixed, paraffin-embedded brain tumor.

In order to minimize the likelihood of cross-hybridization, only LMW RNA was used in the microarray hybridizations. LMW RNA was isolated using a commercially available kit that successfully separated smaller from larger RNA species. The resulting LMW RNAs from the FFPE tissue appeared relatively less degraded than the larger RNAs from FFPE tissue (FIG. 3). It was also considered that miRNAs could be isolated from archival formalin-fixed, paraffin-embedded (FFPE) pathological material since short segments of RNAs have been shown to be preserved in FFPE tissue (Van Deerlin et al., *Neurochem. Res.* 27:993-1003 (2002)), and siRNAs are relatively slow to degrade in vivo (Chiu et al., *Mol. Cell.* 10:549-561 (2002)).

To directly compare the performance of RAKE with RNA isolated from fresh or FFPE material, tissue was obtained from a surgically removed human brain tumor (anaplastic oligodendroglioma). RNA was isolated from half of the specimen and the other half of the specimen was submitted for routine FFPE processing. RNA was then isolated from 50 μM-thick serial sections from the paraffin block. Consistent with prior studies, RNA prepared from fresh tissue appeared to be less degraded than that of FFPE tissue (FIG. 3). It was also found that an appreciable amount of total RNA (up to 10 μgrams) could be isolated from a single 50 μM-thick section of FFPE tissue.

RAKE Analysis on Tissue Cultured, FFPE, and Fresh Brain Tumor RNA.

Specimens were analyzed using three replicates for all RNA samples: biological replicates for HeLa and Jurkat cells, and technical replicates for human brain tumor tissue. Technical replicates were performed on the human brain tumors. A statistically definitive miRNA profile for individual tumor types will result from further analyses of more human data. Valid conclusions about the RNA sampled in the replicates is set forth in greater detail elsewhere herein.

Figure 4:
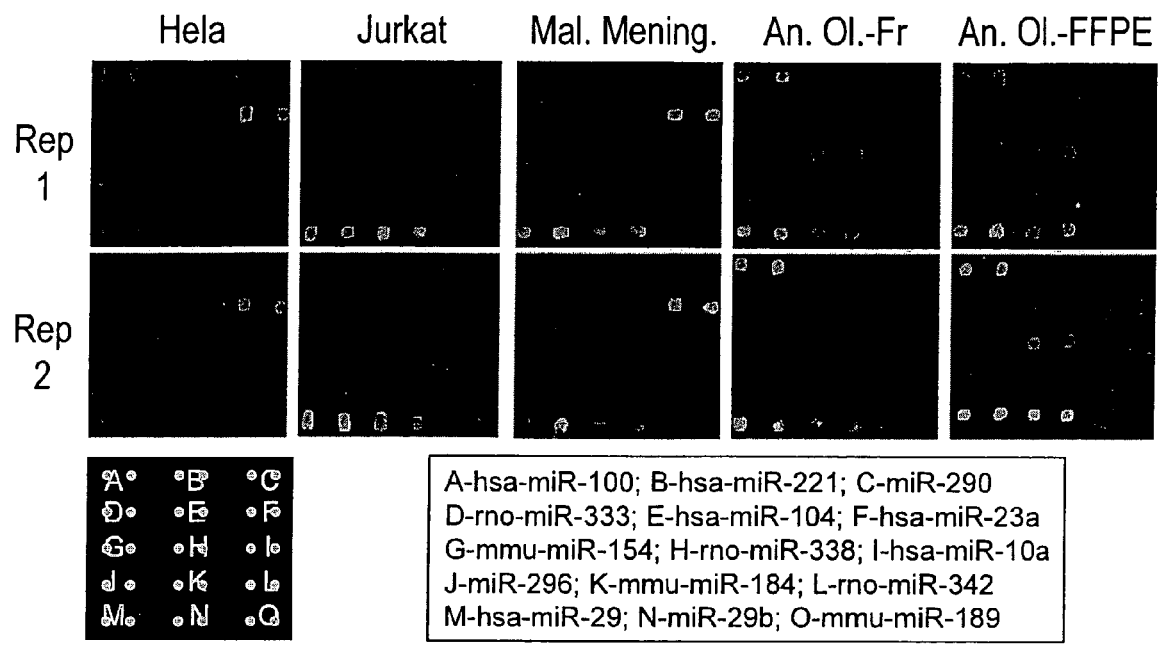
FIG. 4 contains a series of representative images from RAKE assays. Samples are indicated on top. Rep 1, Rep 2: replicates. Position and identity of the spotted probes are shown on the bottom.

Most negatively-hybridizing spots exhibited less of a signal, as compared with background (FIG. 4). Signal was defined as the median of foreground spot fluorescence at 532 nm wavelength, minus background (defined by surrounding pixel intensity). Negative values were normalized to zero. Otherwise, no normalization was used since there was only a single dye, the number of samples was only 239, and values were consistent across the microarray slides, as described elsewhere herein. A summary of the mean of the three replicates for all five samples (RNA from HeLa cells, Jurkat cells, malignant meningioma, and fresh and FFPE-derived anaplastic oligodendroglioma tissue) is presented in FIG. 5. Results from duplicated miRNAs, ath-miRNAs, and other controls suggest that only ath-miR-319 showed nonspecific signal (positive in some experiments without RNA targets), due to a technical problem with this particular probe.

Figure 6A:
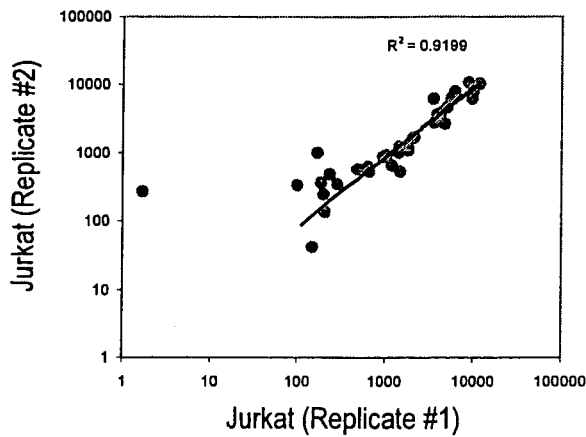
FIGS. 6A-6C graphically compare results from RAKE assays between different samples. Numbers on the ordinate and abscissa relate to signal intensities in reference to individual miRNAs (spots).
Figure 6:
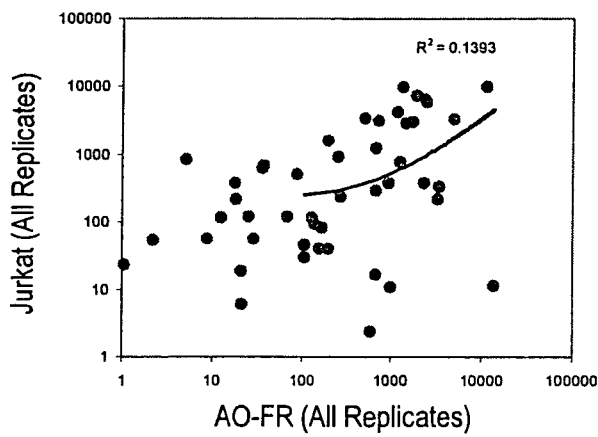
Figure 6C:
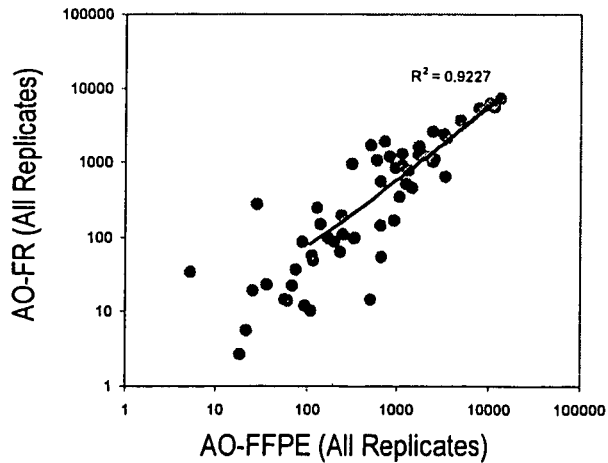

The DNA spike-in oligonucleotides produced high signal, as expected. Some miRNAs demonstrated high signal in multiple tissues (e.g., miR-15, miR-16, let-7f), whereas others were relatively restricted to certain tissue types (e.g., miR-27b in HeLa cells (SEQID No:4), miR148 in Jurkat cells, miR-199b in malignant meningioma, and miR-9 in the fresh and FFPE anaplastic oligodendroglioma). Biological and technical replicates were highly correlated (with coefficients of correlation, $R^2 > 0.9$). Representative examples are shown in FIG. 6. Note also that the fresh and FFPE anaplastic oligodendroglioma showed results that were highly correlated ($R2>0.9$) with each other, showing that formalin fixation and paraffin embedding did not significantly skew the miRNA profile.

Northern Blot Validation.

Northern blots were used to evaluate selected data obtained by RAKE (FIG. 7). These experiments were performed on total RNA. Although the results were for the most part the same between RAKE and the Northern blots, there was some discrepancy. The largest discrepancy was for miR-23b, which by Northern blots showed robust signal for both HeLa and malignant meningioma derived RNA. RAKE showed no detectable amounts of miR-23b in all samples. These results suggest that miR-23b expression was indeed low or absent in these tissues. However, in Northern blots, the miR-23b DNA oligonucleotide probe might cross-hybridize with the paralogous miRNA, miR-23a (miR-23a: 5'-aucacauugccaggga-uuucc (SEQ ID NO:1); mir23b: 5'-aucacauugccagggauuac-cac (SEQ ID NO:2). By contrast, the RAKE assay discriminated the difference between miR-23a and miR-23b because, like many paralogs, miR-23a and miR-23b differ at their 3' end. Consequently, they could only prime Klenow extension when they were hybridized to the appropriate, specific probe.

Discrimination of Paralogous miRNA's that Differ at the 3'-end.

To further test the ability of RAKE to discriminate between paralogous miRNAs, parallel microarray and Northern blot experiments were performed on three separate paralogous miRNA pairs (FIG. 8A, SEQID Nos:1, 2 and 4-7) that differed primarily at their 3'-ends (most differences between miRNA paralogs are found at the 3'-ends). Each paralogous miRNA (0.1 pmoles; $6 \times 10^{10}$ molecules) was analyzed by RAKE and on Northern blots (FIGS. 8B, 8C). The mean signal intensity (expressed in log units) for each miRNA was determined in RAKE (n=1.2) and in Northern blots (n=2). A ratio between the paralogous miRNAs was calculated for each pair (shown in FIG. 8D). The results of this analysis showed that RAKE is superior to Northern blots in discriminating miRNA paralogs.

For example, the power of RAKE to discriminate between hsa-miR-23a/23b paralogs in a sample containing hsa-miR-23a (SEQID No:1), was 9.6 times (=13.9/1.44) that of the Northern blots. Similarly, the power of RAKE to discriminate between hsa-miR-23a/23b paralogs in a sample containing hsa-miR-23b (SEQID No:2), was 10.6 times (0.85/0.08) that of the Northern blots. These values are somewhat different for each miRNA paralog tested in FIG. 8. It was likely due to at least two factors. First, the number, identity and position of the nucleotide differences between the paralogous miRNAs, may have influenced their hybridization properties. Second, the use of B-dATP in the RAKE assay may have reduced its power to discriminate between certain miRNA paralogs. As described above (FIG. 1), B-dATP was used along with Klenow enzyme to extend hybridized miRNAs. When hsa-miR-200b (present in the sample RNA) hybridized to the mmu-miR-200b probe (which is the antisense DNA sequence of mmu-miR-200b (SEQID No:7)), the Klenow enzyme incorporated a single B-dATP molecule on the hsa-miR-200b (SE-QID No:6). This is because the mmu-miR-200b probe contains a thymidine corresponding to the adenine (underlined in FIG. 8A) found in the 3'-end of mmu-miR-200b, but not found in hsa-miR-200b.

For the same reason, hsa-miR-23a (SEQID No:1) gave a weak signal on RAKE on the hsa-miR-23b (SEQID No:2) spot (FIGS. 8A, B). In contrast, up to three B-dATP molecules may be incorporated when hsa-miR-200b hybridizes to its own probe (because there are three consecutive thymidines, corresponding to "Spacer sequences" (FIG. 1, SEQID No:3) after the 3'-end of the hsa-miR-200b DNA probe SEQID No:6), leading to a stronger signal on RAKE. This also applies to hsa-miR-23a (SEQID No:1) when hybridized to its own probe. Nevertheless, RAKE is still superior to Northern blots in discriminating paralogous miRNAs differing at the 3'-ends (FIG. 8D). The discriminating power of RAKE towards paralogous miRNAs that differ by the presence of additional adenine(s) at their 3'-ends (such as, hsa-miR-23b (SEQID No:2) versus hsa-miR23a (SEQID No:2), also may be improved by using B-dNTPs, other than dATP, and modifying the sequences of the spacer accordingly.

Accordingly, the invention has established a microarray platform to enable high-throughput gene expression analyses of small RNAs. In addition, the RAKE assay may have applications besides miRNA gene expression profiling, and the ability to apply the Klenow enzyme (with high sensitivity and specificity) as a RNA or DNA-primed polymerase on a microarray slide will open the door to further interesting studies including, for example, viral gene expression profiling.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. An assay method for analyzing a nucleic acid sample, the assay method comprising;
   obtaining a single-stranded nucleic acid sample comprising at least one target RNA having an unknown expression profile;
   immobilizing onto a substrate at least one known single-stranded oligonucleotide hybridization probe, to provide at least one immobilized probe template, the probe comprising a nucleotide sequence complementary to the at least one target RNA in the single-stranded nucleic acid sample, wherein the nucleotide sequence is followed 5' by consecutive thymidine nucleotides;
   hybridizing the at least one target RNA to the complementary nucleotide sequence of the at least one immobilized probe template under hybridization conditions, to provide at least one hybridized target RNA, thereby producing at least one double-stranded substrate-immobilized hybridized nucleic acid comprising the at least one hybridized target RNA and the at least one immobilized probe template, wherein the at least one hybridized target RNA is a at least one hybridized target RNA primer and the at least one immobilized probe template is a at least one template for template directed synthesis; then washing the substrate containing the substrate-immobilized hybridized nucleic acid;
   incubating the at least one substrate-immobilized hybridized nucleic acid with polymerase to catalyze the addition of at least one labeled complementary nucleotide onto the 3' end of the at least one hybridized target RNA primer, producing a primed extension product comprising at least one incorporated nucleotide, wherein the at least one incorporated nucleotide is the at least one labeled complementary nucleotide; then washing to remove non-hybridized and unincorporated nucleotides;
   incubating the washed, primed extension product with a fluorescent, luminescent or radioactive detection reagent that binds to the at least one labeled complementary nucleotide on the primed extension product;
   imaging the resulting extension product and signals from the detection reagent bound thereto; and
   identifying image intensities to determine if a recognition image intensity is present, indicating hybridization between the at least one target RNA and the at least one immobilized probe template.

2. The method of claim 1, further comprising quantifying abundance of the at least one target RNA in the sample targeted by the at least one immobilized probe.

3. The method according to claim 2, wherein the single-stranded nucleic acid sample comprises at least one microRNA.

4. The method according to claim 1, wherein the at least one incorporated nucleotide comprises a biotin label.

5. The method according to claim 2, wherein the at least one double-stranded substrate-immobilized hybridized nucleic acid is RNA/DNA.

6. The method according to claim 1, further comprising adding an exonuclease to hydrolyze a single-stranded probe template which does not hybridize to the at least one target RNA.

7. The method according to claim 6, wherein the exonuclease is Exonuclease I.

8. The method according to claim 1, wherein the polymerase is Klenow DNA polymerase.

9. The method according to claim 1, wherein the luminescent label used to label the hybridized nucleic acids is a fluorophore.

10. The method according to claim 9, wherein the fluorophore is a streptavidin-conjugated fluorophore.

11. The method of claim 1, wherein the substrate is a glass micro array slide.

12. The method claim 1, providing high-throughput expression profiling.

13. The method of claim 3, further comprising expression profiling the at least one microRNA based upon the resulting hybridization pattern.

14. The method of claim 3, further comprising viral gene expression profiling based upon the resulting hybridization pattern.

15. The method of claim 1, wherein absence of recognition image intensity indicates absence of hybridization between the at least one immobilized probe template and the at least one target RNA.

16. The method of claim 1, wherein depending upon the hybridization templates that are immobilized, the assay permits simultaneously detecting multiple target RNAs in the sample.

17. The method of claim 1, wherein the assay is an RNA-primed Array-based Klenow Enzyme (RAKE) assay.

18. The method of claim 17, providing high-throughput expression profiling.

19. The method of claim 17, providing viral gene expression profiling.

* * * * *

SEQUENCE LISTING

```
<160> NUMBER OF SEQ ID NOS: 7

<210> SEQ ID NO 1
<211> LENGTH: 21
<212> TYPE: RNA
<213> ORGANISM: Artificial sequence
<220> FEATURE:
<223> OTHER INFORMATION: synthetic probe

<400> SEQUENCE: 1
aucacauugc cagggauuuc c                                              21

<210> SEQ ID NO 2
<211> LENGTH: 23
<212> TYPE: RNA
<213> ORGANISM: Artificial sequence
<220> FEATURE:
<223> OTHER INFORMATION: synthetic probe

<400> SEQUENCE: 2
aucacauugc cagggauuac cac                                            23

<210> SEQ ID NO 3
<211> LENGTH: 46
<212> TYPE: DNA
<213> ORGANISM: Artificial sequence
<220> FEATURE:
<223> OTHER INFORMATION: synthetic probe

<400> SEQUENCE: 3
gtcgtgactg ggaatagcct gtttaactat acaacctact acctca                   46

<210> SEQ ID NO 4
<211> LENGTH: 22
<212> TYPE: RNA
<213> ORGANISM: Artificial sequence
<220> FEATURE:
<223> OTHER INFORMATION: synthetic probe

<400> SEQUENCE: 4
uucacagugg cuaaguuccg cc                                             22

<210> SEQ ID NO 5
<211> LENGTH: 20
<212> TYPE: RNA
<213> ORGANISM: Artificial sequence
<220> FEATURE:
<223> OTHER INFORMATION: synthetic probe

<400> SEQUENCE: 5
```

```
uucacagugg cuaaguucug                                              20

<210> SEQ ID NO 6
<211> LENGTH: 24
<212> TYPE: RNA
<213> ORGANISM: Artificial sequence
<220> FEATURE:
<223> OTHER INFORMATION: synthetic probe

<400> SEQUENCE: 6
cucuaauacu gccugguaau gaug                                         24

<210> SEQ ID NO 7
<211> LENGTH: 23
<212> TYPE: RNA
<213> ORGANISM: Artificial sequence
<220> FEATURE:
<223> OTHER INFORMATION: synthetic probe

<400> SEQUENCE: 7
uaauacugcc ugguaaugau gac                                          23
```